(12) United States Patent
Soyemi et al.

(10) Patent No.: US 7,532,919 B2
(45) Date of Patent: May 12, 2009

(54) MEASURING TISSUE OXYGENATION

(75) Inventors: Olusola O. Soyemi, Longmont, CO (US); Babs R. Soller, Northboro, MA (US); Ye Yang, Worcester, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 11/755,643

(22) Filed: May 30, 2007

(65) Prior Publication Data

US 2008/0097173 A1    Apr. 24, 2008

Related U.S. Application Data

(60) Provisional application No. 60/809,238, filed on May 30, 2006.

(51) Int. Cl.
*A61B 5/1455* (2006.01)
(52) U.S. Cl. .................................... 600/323
(58) Field of Classification Search ............. 600/310, 600/322, 323, 330, 336
See application file for complete search history.

(56) References Cited

U.S. PATENT DOCUMENTS

| | | | | |
|---|---|---|---|---|
| 5,297,548 A | * | 3/1994 | Pologe | 600/310 |
| 5,490,506 A | * | 2/1996 | Takatani et al. | 600/309 |
| 5,517,987 A | * | 5/1996 | Tsuchiya | 600/328 |
| 5,931,779 A | * | 8/1999 | Arakaki et al. | 600/310 |

* cited by examiner

*Primary Examiner*—Eric F Winakur
(74) *Attorney, Agent, or Firm*—Fish & Richardson P.C.

(57) ABSTRACT

Methods and systems for calculating tissue oxygenation, e.g., oxygen saturation, in a target tissue are disclosed. In some embodiments, the methods include: (a) directing incident radiation to a target tissue and determining reflectance spectra of the target tissue by measuring intensities of reflected radiation from the target tissue at a plurality of radiation wavelengths; (b) correcting the measured intensities of the reflectance spectra to reduce contributions thereto from skin and fat layers through which the incident radiation propagates; (c) determining oxygen saturation in the target tissue based on the corrected reflectance spectra; and (d) outputting the determined value of oxygen saturation.

37 Claims, 6 Drawing Sheets

MEASURING TISSUE OXYGENATION

CROSS-REFERENCE TO RELATED APPLICATIONS

This application claims priority to U.S. Provisional Application Ser. No. 60/809,238 entitled "Measuring Tissue Oxygen Saturation," filed on May 30, 2006, the entire contents of which are incorporated herein by reference.

STATEMENT AS TO FEDERALLY SPONSORED RESEARCH

This invention was made with Government support under U.S. Army Medical Research Command Grant Number W81XWH-06-1-0545, and National Space Biomedical Research Institute Grant Number SMS00205, which is funded under NASA Cooperative Agreement Number NCC 9-58. The Government has certain rights in this invention.

TECHNICAL FIELD

This invention relates to measuring properties such as oxygen saturation in tissues.

BACKGROUND

Tissue oxygen saturation ($SO_2$) provides a measure of oxygen content in red blood cells. Measurement of $SO_2$ in tissue can be used to assess micro-vascular circulation and oxygen supply to tissue cells arising from certain pathologic conditions such as sepsis and diabetes, for example, which result in impaired vascular blood flow. Tissue $SO_2$ measurements can also be used in exercise physiology, where a mismatch between oxygen demand and supply during periods of exercise can be used to determine an extent of physical conditioning of a subject.

Infrared reflectance measurements can be used for non-invasive, quantitative detection of various chemical species in tissue. For example, interrogation of oxygenated and non-oxygenated hemoglobin in tissue can be made via reflectance measurements of the tissue at wavelengths that fall within a range of about 700-1000 nm. In this wavelength range, many chemical species that may be present in the tissue and which are not of interest interact only weakly with incident radiation, and signals arising from hemoglobin can be isolated from signals that arise from other chemical components. Infrared radiation typically penetrates relatively deeply into tissues, and can be used to probe underneath surface tissues such as skin and fat to measure analytes of interest in deeper muscle and other internal tissues. Suitable systems for performing infrared reflectance measurements in tissue are described, for example, in U.S. Publication Number US 2007/0038041 entitled "SYSTEMS AND METHODS FOR CORRECTING OPTICAL REFLECTANCE MEASUREMENTS," filed on Apr. 25, 2006, the entire contents of which are incorporated herein by reference.

SUMMARY

Disclosed herein are systems and methods for determining tissue oxygen saturation ($SO_2$) and other quantities such as oxygen tension from infrared spectroscopic measurements. The systems and methods are based, at least in part, on an approach to calculating oxygen saturation in tissue based on an equation for light attenuation by the tissue, where the equation includes terms that correspond to light absorption and scattering by components of the tissue. One form of a light attenuation equation is based on a series expansion (e.g., a Taylor series expansion) of a measured light attenuation spectrum and Beer's law, and includes light attenuation terms that correspond to: absorption by oxygenated heme (hemoglobin and myoglobin), non-oxygenated heme, water, and other chromophores present in the tissue; scattering in the tissue; and a constant factor that arises from experimental conditions. These contributions can be quantitatively determined by a two-stage numerical fitting procedure, which yields concentrations of oxygenated and non-oxygenated heme in the tissue. Tissue oxygen saturation can then be determined from the concentrations of oxygenated and non-oxygenated heme. Other quantities can also be determined from measurements of $SO_2$. For example, oxygen tension ($PO_2$) can be determined from a mathematical equation that relates $PO_2$ to $SO_2$.

Tissue oxygen saturation and/or oxygen tension can function as important physiological diagnostic and/or predictive indicators. In particular, $SO_2$ is a sensitive probe of capillary vasoconstriction, and can be used to track progression and/or treatment of conditions that result in a variation in blood volume in the tissue, or vasoconstriction/vasodilation in response to an insult. Examples of such conditions are hemorrhage, sepsis, heart disease, and diabetes.

In general, in one aspect, the invention features a method for calculating oxygen saturation in a target tissue, where the method includes: (a) directing incident radiation to a target tissue and determining reflectance spectra of the target tissue by measuring intensities of reflected radiation from the target tissue at a plurality of radiation wavelengths; (b) correcting the measured intensities of the reflectance spectra to reduce contributions thereto from skin and fat layers through which the incident radiation propagates; (c) determining oxygen saturation in the target tissue based on the corrected reflectance spectra; and (d) outputting the determined value of oxygen saturation.

Embodiments of the method can include one or more of the following features. Determining oxygen saturation can include determining light attenuation spectra from the corrected reflectance spectra, and calculating oxygen saturation based on concentrations of oxygenated and deoxygenated heme in the target tissue that are derived from the light attenuation spectra, where heme includes hemoglobin and myoglobin in the target tissue. The concentrations of oxygenated and deoxygenated heme can be derived from the light attenuation spectra by fitting the light attenuation spectra to a model light attenuation equation. The light attenuation equation can include a Beer's Law equation that includes terms that correspond to incident light absorption by oxygenated heme, deoxygenated heme, and water in the target tissue. For example, the light attenuation equation can include a series expansion (e.g., a Taylor series expansion) of light attenuation in a plurality of terms that correspond to Beer's Law absorption terms. The fitting can be performed automatically by a processor.

The light attenuation equation can include a term that varies linearly with a wavelength of the incident light, the term having a functional form $a\lambda$ where a is a constant and $\lambda$ is the wavelength of the incident light. The value of a can be constrained during fitting so that a assumes only values that are less than or equal to zero. The light attenuation equation can include a constant term independent of the wavelength of the incident light.

Fitting the light attenuation spectra to a model can include performing a two-stage fitting procedure where, in a first stage, initial values of one or more model parameters are determined, and in a second stage, the light attenuation spectra are fitted to the model, where the model includes the initial parameter values determined in the first stage. The light attenuation spectra can be fitted to the model by minimizing a sum of squared differences between the light attenuation spectra and light attenuation values determined from the model.

The light attenuation equation can include a baseline function derived from a difference between light attenuation values determined from the light attenuation equation and the light attenuation spectra. The light attenuation equation can include a differential path length factor that varies directly with a scattering coefficient of the target tissue and inversely with an absorption coefficient of the target tissue. The light attenuation equation can include a diffuse reflectance equation derived from a radiation diffusion model of incident light in the target tissue.

Measuring intensities of reflected radiation can include: (a) measuring, along a first optical path from a light source to a detector, reflected radiation from the target tissue that corresponds to a first source-detector spacing; and (b) measuring, along a second optical path from the light source to the detector, reflected radiation from the target tissue that corresponds to a second source-detector spacing different from the first source-detector spacing. The reflected radiation measured at the first source-detector spacing can include a first weighting of contributions from the target tissue and from tissue layers disposed between the light source and the target tissue, and the reflected radiation measured at the second source-detector spacing can include a second weighting of contributions from the target tissue and from the tissue layers disposed between the light source and the target tissue different from the first weighting. The tissue layers disposed between the light source and the target tissue can be skin and fat layers. Correcting the measured intensities of the reflectance spectra can include reducing contributions from the skin and fat layers to the reflected radiation measured at the second source-detector spacing based on the reflected radiation measured at the first source-detector spacing.

The method can include determining oxygen tension in the target tissue based on oxygen saturation in the target tissue. The method can include assessing a level of vasoconstriction in a patient based on a measurement of total hemoglobin in a target tissue of the patient, where total hemoglobin is determined based on the concentrations of oxygenated and deoxygenated heme in the target tissue.

The target tissue can be within a human. The target tissue can be within an animal. The target tissue can be a muscle tissue.

The plurality of wavelengths can include at least 100 wavelengths or more. The plurality of wavelengths can include wavelengths from 700 nm to 1000 nm (e.g., wavelengths from 725 nm to 880 nm).

Embodiments of the method can also include any of the other method steps disclosed herein, as appropriate.

In another aspect, the invention features a method of monitoring blood volume in a patient, where the method includes: (a) directing incident radiation to a target tissue of the patient and determining reflectance spectra of the target tissue by measuring intensities of reflected radiation from the target tissue at a plurality of wavelengths; (b) correcting the measured intensities of the reflectance spectra to reduce contributions thereto from skin and fat layers through which the incident radiation propagates; (c) determining total heme concentration in the target tissue based on the corrected reflectance spectra; (d) assessing a blood volume in the patient based on the total heme concentration; and (e) outputting the assessed blood volume.

Embodiments of the method can include the following features.

The method can include assessing a stage of progress of at least one of hemorrhage, sepsis, heart disease, and diabetes in the patient based on the assessed blood volume. Embodiments of the method can also include any of the other method steps disclosed herein, as appropriate.

In a further aspect, the invention features a method for calculating oxygen saturation in a target tissue, where the method includes: (a) directing incident radiation to a target tissue and determining reflectance spectra of the target tissue by measuring intensities of reflected radiation from the target tissue at a plurality of radiation wavelengths; (b) determining light attenuation spectra of the target tissue from the reflectance spectra, and fitting the light attenuation spectra to a model light attenuation equation; and (c) determining oxygen saturation in the target tissue based on the fitting of the light attenuation spectra. Fitting the light attenuation spectra to a model can include performing a two-stage fitting procedure where, in a first stage, initial values of one or more model parameters are determined, and in a second stage, the light attenuation spectra are fitted to the model, where the model includes the initial parameter values determined in the first stage.

Embodiments of the method can include the following features.

The model can include a term having a functional form $a\lambda$, and where the value of a is constrained during the fitting to be less than or equal to zero. Embodiments of the method can also include any of the other method steps disclosed herein, as appropriate.

In another aspect, the invention features a system that includes a light source configured to direct incident radiation to a target tissue, a detector, and a processor coupled to the detector and configured to: (a) determine reflectance spectra of the target tissue; (b) correct the reflectance spectra to reduce contributions thereto from skin and fat layers through which the incident radiation propagates; and (c) determine oxygen saturation in the target tissue based on the corrected reflectance spectra.

Embodiments of the system can include one or more of the following features.

The processor can be configured to determine reflectance spectra of the target tissue by directing the detector to measure intensities of reflected radiation from the target tissue at a plurality of radiation wavelengths. The processor can be configured to determine oxygen saturation by calculating light attenuation spectra from the corrected reflectance spectra, and calculating oxygen saturation based on concentrations of oxygenated and deoxygenated heme in the target tissue that are derived from the light attenuation spectra, where heme includes hemoglobin and myoglobin in the target tissue.

The system can also include: (a) a first radiation path between the light source and the detector, and corresponding to a first distance between the light source and the detector; and (b) a second radiation path between the light source and the detector, and corresponding to a second distance between the light source and the detector different from the first distance. Incident radiation from the light source can be directed along each of the first and second radiation paths to the target tissue, and reflected radiation from the target tissue can be directed along each of the first and second radiation paths to the detector. The processor can be configured to reduce contributions to the measured reflectance spectra from skin and fat layers by measuring reflectance spectra along each of the first and second light paths, and combining the reflectance spectra to produce corrected reflectance spectra. Each of the first and second radiation paths can include an optical fiber.

The processor can be configured to derive the concentrations of oxygenated and deoxygenated heme in the target tissue by fitting the light attenuation spectra to a model light attenuation equation. The model light attenuation equation can include a Beer's Law equation that includes terms that correspond to absorption of incident radiation by oxygenated heme, deoxygenated heme, and water in the target tissue.

The processor can be configured to determine oxygen tension in the target tissue from oxygen saturation. The processor can be configured to determine total heme concentration in the target tissue from the concentrations of oxygenated and deoxygenated heme in the target tissue. The processor can be configured to assess a blood volume in the target tissue based on the total heme concentration.

The processor can also be configured to perform any of the other method steps disclosed herein, as appropriate.

Embodiments can include one or more of the following advantages.

Oxygen saturation and/or oxygen tension are determined based on light attenuation measurements performed in the infrared region of the electromagnetic spectrum. The effects of absorption and scattering due to analytes other than heme are smaller in this region than in other spectral regions. As a result, heme absorption can be quantitatively isolated from absorption and scattering processes due to other tissue components.

Further, the infrared radiation can penetrate relatively deeply into a patient, interrogating tissue (e.g., muscle tissue) that is located underneath layers of skin and fat. The penetration depth of the infrared radiation permits measurement of oxygen saturation in muscle tissues, for example, which are typically located relatively deeply underneath layers of skin and fat. The infrared spectral data can be corrected for light absorption by skin pigments and light scattering by fat, thereby permitting even more accurate quantitative determination of heme absorption than would otherwise be possible without such corrections. The effects of water absorption in a patient's tissue can also be quantitatively determined and separated from heme absorption.

Measurements are performed across a relatively large number of wavelength channels such as 100 wavelength channels or more (e.g., 150 wavelength channels or more, 200 wavelength channels or more, 400 wavelength channels or more, 600 wavelength channels or more, 1000 wavelength channels or more). The relatively large number of measurements improves the signal-to-noise ratio of the measured data relative to instruments that record data from, for example, between two and six wavelength channels.

The measurements disclosed herein are performed non-invasively using a low cost, portable measurement system. Results can be displayed in real-time or near real-time, which enables continuous monitoring of oxygen saturation and/or oxygen tension. Where these parameters are correlated with a particular medical condition in a patient, the progress of the condition can be evaluated in real-time. The instruments can operate with manual intervention, or in fully automatic mode without operator intervention.

Fitting parameters can be constrained appropriately to enable more accurate quantitative separation of scattering and absorption processes. For example, coefficients of certain wavelength-dependent scattering terms can be constrained to take only non-positive values during fitting of the attenuation equation to measured light attenuation data, to correlate with typical variations in tissue scattering as a function of light wavelength. Appropriate choices of fitting constraints can enable improved quantitative separation of the effects of in vivo tissue scattering and absorption by oxygenated heme.

The light attenuation equation can be fitted to measured data in a two-stage fitting procedure. A first stage of the fitting procedure determines initial values of certain fitting parameters, and a second stage of the fitting procedure determines a lowest-error fit of the measured data to the attenuation equation, starting from the initial values determined in the first stage. The two-stage fitting procedure enables fitting of measured spectral data without intervention by an operator, and reduces the overall time required to perform the fitting procedure. In certain embodiments, the two-stage fitting procedure can also improve the accuracy of the fitting results relative to one-step fitting algorithms.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will be apparent from the description, drawings, and claims.

DESCRIPTION OF DRAWINGS

Like reference symbols in the various drawings indicate like elements.

DETAILED DESCRIPTION

Disclosed herein are methods and systems for obtaining measurements of tissue oxygen saturation and other physiological quantities such as oxygen tension from infrared reflectance spectra of a target tissue (e.g., a tissue in a human or an animal). Values of these quantities are derived by analyzing a light attenuation model that accounts for tissue absorption and scattering. Reflectance spectra of a target tissue are first measured by a suitably configured spectrometer system, and then the spectra are analyzed, for example, by a processor coupled to the spectrometer system.

Measurement Systems

Figure 1:
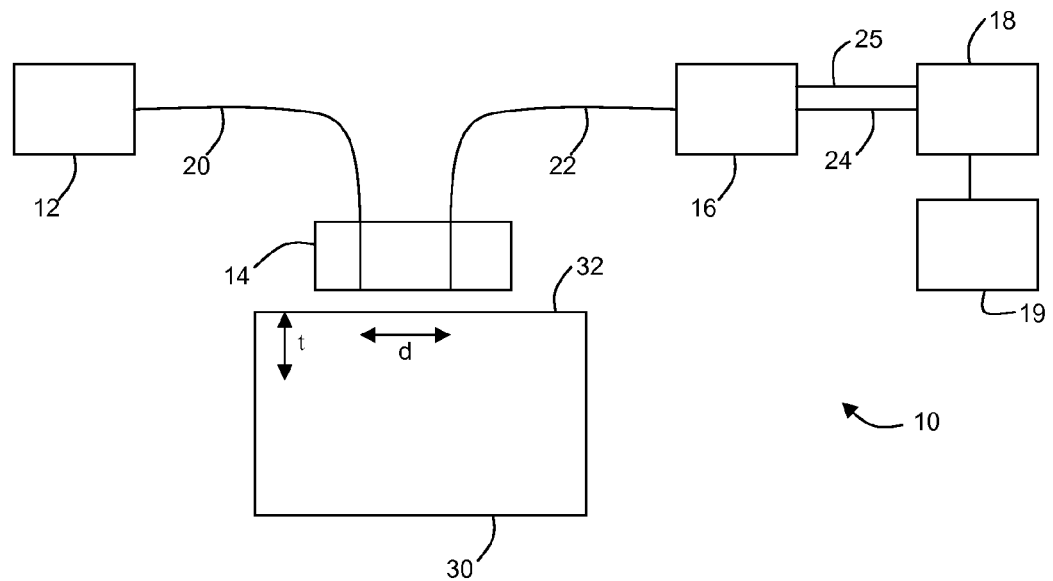
FIG. 1 is a schematic diagram of one possible embodiment of a spectrometer system for measuring oxygen saturation in a target tissue.

A variety of measurement systems can be used to measure attenuation by a target tissue of incident light in the infrared region of the electromagnetic spectrum. FIG. 1 shows a schematic diagram of one embodiment of such a measurement system. Measurement system 10 includes a light source 12, a probe head 14, a detector 16, a processor 18, and a display 19. Light source 12 provides radiation which is coupled into light path 20 and propagates along light path 20 from light source 12 to probe head 14. The radiation emerges from light path 20 and is incident on a surface 32 of a target tissue 30 adjacent to probe head 14. A portion of the incident radiation is reflected by target tissue 30 and enters light path 22. The reflected radiation propagates along light path 22 to detector 16. Detector 16 is configured to measure an intensity of the reflected radiation, as a function of wavelength. Processor 18, e.g., a stand-alone processor or a portion of an external computer system, coupled to detector 16 via communication line 24, provides configuration signals to detector 16. In addition, processor 18 is configured to receive, via communication line 25, the spectral reflectance intensity data recorded by detector 16. Processor 18 can be configured to transform the spectral reflectance data into light attenuation data, for example, that measures wavelength-dependent attenuation of the incident radiation by target tissue 30. As shown in FIG. 1, processor 18 is in electrical communication with display 19. Spectral reflectance data, wavelength-dependent light attenuation data, and/or other data or physiological quantities determined from the measured data, can be output from processor 18 to display 19. Alternatively, or in addition, measured and/or calculated data can be output from processor 18 to another processor (not shown) for further processing, to a storage medium, or to another device (e.g., a computer and/or a wireless communications device).

The ends of light paths 20 and 22 are separated by a distance d in probe head 14. In some embodiments, the distance d can be relatively short, such as about 5 mm or less (e.g., about 4 mm or less, about 3 mm or less, about 2 mm or less, or about 1 mm or less). In other embodiments, the distance d can be relatively long, such as about 20 mm or more (e.g., about 25 mm or more, about 30 mm or more, about 35 mm or more). In certain embodiments, probe head 14 is configured to permit adjustment of the distance d by a system operator. For example, the distance d can be adjusted to acquire spectral data that includes contributions from tissues within a certain depth t of surface 32 of target tissue 30 adjacent to probe head 14. In general, the larger the distance d, the greater the depth of tissue t contributing to the measured light attenuation data.

Light source 12 can, in general, include a wide variety of sources. For example, light source 12 can include an incandescent source, one or more light-emitting diodes, a laser-based source, or other types of sources. Light source 12 can provide radiation in one or more selected regions of the electromagnetic spectrum, such as the ultraviolet region, the visible region, the infrared region, or other regions. In some embodiments, for example, light source 12 is configured to provide radiation in the infrared region of the electromagnetic spectrum. The radiation can include wavelengths from about 700 nm to about 1000 nm, for example.

In certain embodiments, the radiation provided by light source 12 can include multiple wavelengths. For example, a full-width at half maximum of the distribution of wavelengths of the radiation can be about 10 nm or more (e.g., about 20 nm or more, about 50 nm or more, about 100 nm or more, about 150 nm or more, about 200 nm or more, about 250 nm or more). The distribution of wavelengths of the radiation can be produced from a single source element such as an incandescent element or a broadband light emitting diode, for example, or from multiple source elements (e.g., multiple light emitting diodes) operating simultaneously or sequentially.

Light paths 20 and 22 can be formed from materials suitable for directing the radiation provided by light source 12. In certain embodiments, for example, one or both of light paths 20 and 22 can be waveguides formed by one or more optical fibers. In some embodiments, one or both of light paths 20 and 22 can be open passageways formed in probe head 14 and sized to permit the radiation to pass through. In certain embodiments, for example, either or both of light source 12 and detector 16 can be placed in direct contact with the skin of patient, or in direct contact with a target tissue (e.g., without overlying skin and/or fat layers), so that light paths 20 and/or 22 do not include open passageways, but instead include the optical trajectories along which incident and reflected radiation propagate in the target tissue. In some embodiments, one or both of light paths 20 and 22 can include other types of waveguides such as photonic crystal fibers and/or light transmitting polymer materials.

Detector 16 is configured to measure a wavelength-dependent intensity of reflected radiation from target tissue 30. Typically, detector 16 is a spectral detector such as a spectrometer, with a wavelength-dispersing element such as a diffraction grating that is configured for use in a wavelength region that includes the wavelengths in the radiation provided by light source 12. Suitable spectrometers are available, for example, from Ocean Optics Inc. (Dunedin, Fla.). Detector 16 can measure intensities of radiation at multiple wavelengths. For example, in some embodiments, detector 16 is configured to measure the intensity of optical radiation at about 50 or more distinct wavelengths (e.g., about 100 or more distinct wavelengths, about 150 or more distinct wavelengths, about 200 or more distinct wavelengths, about 400 or more distinct wavelengths, about 600 or more distinct wavelengths, about 1000 or more distinct wavelengths).

The spectral intensity data measured by detector 16, which is typically wavelength-dependent reflectance data from target tissue 30, can be converted to wavelength-dependent light attenuation data (e.g., a light attenuation spectrum of target tissue 30) by processor 18 using well known methods. In the subsequent discussion, reference is made to light attenuation spectra of target tissue 30, but the methods and systems disclosed herein can also be used to process spectral reflectance data directly, since the light attenuation and spectral reflectance data are related by a simple mathematical transformation (see, e.g., Equation (2) discussed in the next section).

In addition to converting spectral reflectance data to light attenuation data, processor 18 can be configured to analyze the light attenuation data to obtain measurements of physiologically important quantities such as oxygen saturation and oxygen tension, as will be discussed in further detail below. In general, processor 18 can be configured to perform any of the analysis steps that are discussed herein.

Figure 2:
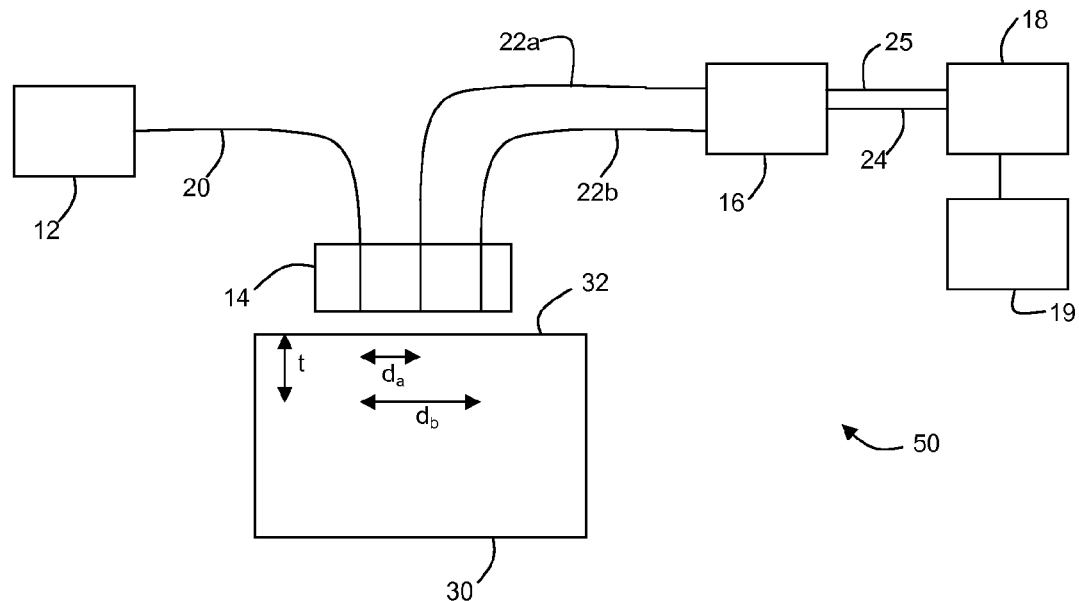
FIG. 2 is a schematic diagram of another embodiment of a spectrometer system for measuring oxygen saturation in a target tissue.

In some embodiments, optical reflectance spectra can be measured at more than one source-detector spacing d. For example, FIG. 2 is a schematic diagram of an embodiment of a measurement system 50 that includes two different source-detector spacings, each of which can be fixed, or adjusted by an operator. Many of the components of measurement system 50 are similar to the components of measurement system 10 and will not be discussed further. Measurement system 50 includes a first detection light path 22a spaced from light path 20 in probe head 14 by a distance $d_a$, and a second detection light path 22b spaced from light path 20 in probe head 14 by a distance $d_b$ greater than $d_a$.

Spectral reflectance measurements can be recorded by detector 16 at multiple source-detector distances to reduce and/or remove the spectral absorption and/or scattering effects of overlying tissue layers from the spectra of underlying tissues of interest. For example, reflectance spectra recorded at the short source-detector distance $d_a$ typically include a first weighting of contributions from tissues near surface 32 and from the deeper interior of target tissue 30 (e.g., primarily from tissues near surface 32 of target tissue 30). Reflectance spectra recorded at the longer source-detector distance $d_b$ typically include a second weighting, different from the first weighting, of contributions from tissues near surface 32 and from the deeper interior of target tissue 30 (e.g., spectra at the longer source-detector distance typically include significant contributions from both tissues near surface 32, and from tissues underlying surface 32). Reflectance data recorded at two different source-detector distances can be processed using suitable algorithms to remove spectral contributions due to overlying tissue layers adjacent to surface 32, retaining primarily spectral contributions due only to the underlying (e.g., deeper) tissue layers. In addition, in some embodiments, the source-detector distances can be adjusted by an operator to improve the selectivity of the spectral reflectance measurements (e.g., to selectively interrogate tissues at particular depths below the surface of a patient's skin).

An as example, in some embodiments, target tissue 30 can include layers of skin and fat proximal to probe head 14, and a muscle tissue of interest that underlies the skin and fat layers (e.g., at a larger distance from probe head 14). Contributions to the light attenuation data that arise from light absorption and/or scattering by the skin (including skin pigments) and fat layers can be reduced or removed from the light attenuation data to improve the accuracy with which the muscle tissue of interest is selectively interrogated. Suitable measurement systems and processing algorithms are disclosed, for example, in U.S. Publication Number US 2007/0038041 entitled "SYSTEMS AND METHODS FOR CORRECTING OPTICAL REFLECTANCE MEASUREMENTS."

In some embodiments, spectral reflectance data at multiple source-detector distances can be measured by systems having a single detection light path and multiple source light paths (e.g., multiple paths for coupling light from one or more radiation sources to probe head 14). In general, the particular configuration of the measurement system does not substantially change the processing algorithms used to remove the spectral effects of overlying tissue layers, nor does it change the analysis algorithms that are used to determine quantities such as oxygen saturation and oxygen tension from the light attenuation spectra.

Having measured spectral reflectance data from target tissue 30 and transformed the data into wavelength-dependent light attenuation data corresponding to the target tissue, processor 18 is configured to analyze the light attenuation data to obtain values of quantities of interest for the target tissue. Various analysis algorithms implemented in processor 18 for obtaining these quantities are disclosed below.

Determination of Oxygen Saturation

In tissue oximetry, infrared radiation can be used to measure the heme component in blood. Although radiation in the visible portion of the electromagnetic spectrum is also absorbed by blood heme, infrared light typically penetrates deeper into tissue, and the effects of light scattering are typically smaller at infrared wavelengths than at visible wavelengths. In muscle cells, for example, myoglobin and hemoglobin are each present in the incident radiation pathway, and each absorbs infrared radiation. In small vessels (e.g., arterioles, capillaries, and venules), changes in infrared absorption primarily reflect changes in concentrations of oxygenated and non-oxygenated heme. As a result, tissue oxygen saturation ($SO_2$) is defined according to the equation $$SO_2 = \frac{c_{(HbO2+MbO2)}}{c_{(HbO2+MbO2)} + c_{(Hb+Mb)}} \quad (1)$$

where $c_{(HbO2+MbO2)}$ is the total concentration of oxygenated heme in the tissue (Hb=hemoglobin, Mb=myoglobin) and $c_{(Hb+Mb)}$ is the total concentration of deoxygenated heme in the tissue. The sum $c_{Hb+Mb}+c_{HbO2+MbO2}$ is the total concentration of heme in the tissue. Hemoglobin and myoglobin have similar absorption profiles through much of the infrared region of the spectrum, and the infrared reflectance measurement techniques disclosed herein are sensitive to both hemoglobin and myoglobin.

A model light attenuation spectrum ($A_{model}(\lambda)$) for a target tissue exposed to incident light is defined in general as the logarithm of the ratio of the incident light intensity and the reflected light intensity. A variety of different models can be used to describe the light attenuation spectrum of a target tissue. In some embodiments, for example, a Taylor series expansion method can be used to express the light attenuation spectrum as a function of one or more absorption terms, as described in Stratonnikov, A. A. and Loschenov, V. B., "Evaluation of blood oxygen saturation in vivo from diffuse reflectance spectra," *Journal of Biomedical Optics* 6: 457-467 (2001). A suitable Taylor series expansion for $A_{model}(\lambda)$ is $$\begin{aligned} A_{model}(\lambda) &= \ln\left(\frac{I_0(\lambda)}{I(\lambda)}\right) \\ &= (c_0 + c_1\lambda) + \ln(10) \cdot \langle L \rangle \cdot \\ &\quad [c_{Hb+Mb}\varepsilon_{Hb}(\lambda) + c_{HbO2+MbO2}\varepsilon_{HbO2}(\lambda) + c_{wat}\varepsilon_{wat}(\lambda)] \end{aligned} \quad (2)$$

where $I_0(\lambda)$ is an incident light intensity (e.g., the light source intensity), $I(\lambda)$ is a reflected light intensity from the tissue, $\lambda$ is a light wavelength, $c_0$ and $c_1$ are constants, <L> is a mean path length of the reflected light through the tissue, $\varepsilon_{Hb}(\lambda)$ is a wavelength-dependent extinction coefficient for deoxygenated hemoglobin, $\varepsilon_{HbO2}(\lambda)$ is a wavelength-dependent extinction coefficient for oxygenated hemoglobin, $c_{wat}$ is a concentration of water in the tissue, and $\varepsilon_{wat}(\lambda)$ is a wavelength-dependent extinction coefficient for water. Hemoglobin and myoglobin have similar extinction coefficients in the infrared region of the spectrum, and so the extinction coefficients of oxygenated and deoxygenated hemoglobin are also used to model myoglobin absorption in Equation (2). The determination of values for the various parameters in Equation (2) is discussed in further detail below.

Typically, it can be difficult to determine the absolute light source intensity $I_0(\lambda)$ under experimental conditions. Accordingly, in some embodiments, reflected light intensity from a 99% reflectance standard, $I_{ref}(\lambda)$, is used in place of $I_0(\lambda)$ when modeling light attenuation. Suitable 99% reflectance standards include, for example, Model SRT-99-050, available from Labsphere, Inc. (North Sutton, N.H.). With the experimental reference light intensity $I_{ref}(\lambda)$ measured instead of $I_0(\lambda)$, the measured light attenuation spectrum, $A_{exp}(\lambda)$, is $$A_{exp}(\lambda) = \ln\left(\frac{I_{ref}(\lambda)}{I(\lambda)}\right) \quad (3)$$

The reference light intensity $I_{ref}(\lambda)$ typically differs from $I_0(\lambda)$ by a wavelength-independent constant factor, which appears as a constant additive contribution to the experimentally-measured light attenuation spectrum of a target tissue. The constant $c_0$ in Equation (2) accounts for this additive contribution to the light attenuation spectrum. In addition, $c_0$ also accounts for wavelength-independent absorption and/or scattering by chromophores and other species in the target tissue other than hemoglobin, myoglobin, and water. Similarly, the constant $c_1$ accounts for wavelength-dependent light absorption and/or scattering from chromophores and other species in the target tissue other than hemoglobin, myoglobin, and water. Terms on the right-hand side of Equation (2) which are multiplied by <L> account for attenuation of incident light by hemoglobin, myoglobin, and water in the target tissue.

Typically, light attenuation in the target tissue can arise from both light absorption and light scattering processes. For example, light is absorbed by hemoglobin in small blood vessels and myoglobin in cells, by both intravascular and extravascular water, and by melanin pigments in skin. Light can be scattered by physical structures such as blood vessels and muscle fibers, and also by fat which overlies muscle tissue of interest (e.g., fat that is disposed between a probe head of a measurement system and the muscle tissue).

The systems and methods disclosed herein can generally be applied to the calculation of oxygen saturation and other physiological quantities in many different types of tissue, including muscle tissue and non-muscle tissue, and any of the steps discussed in connection with the determination of $SO_2$ can also be performed to calculate $SO_2$ in both muscle tissue and non-muscle tissue. Measuring oxygen saturation in muscle tissue provides a particularly sensitive diagnostic indicator of vasoconstriction/vasodilation, for example.

Figure 3:
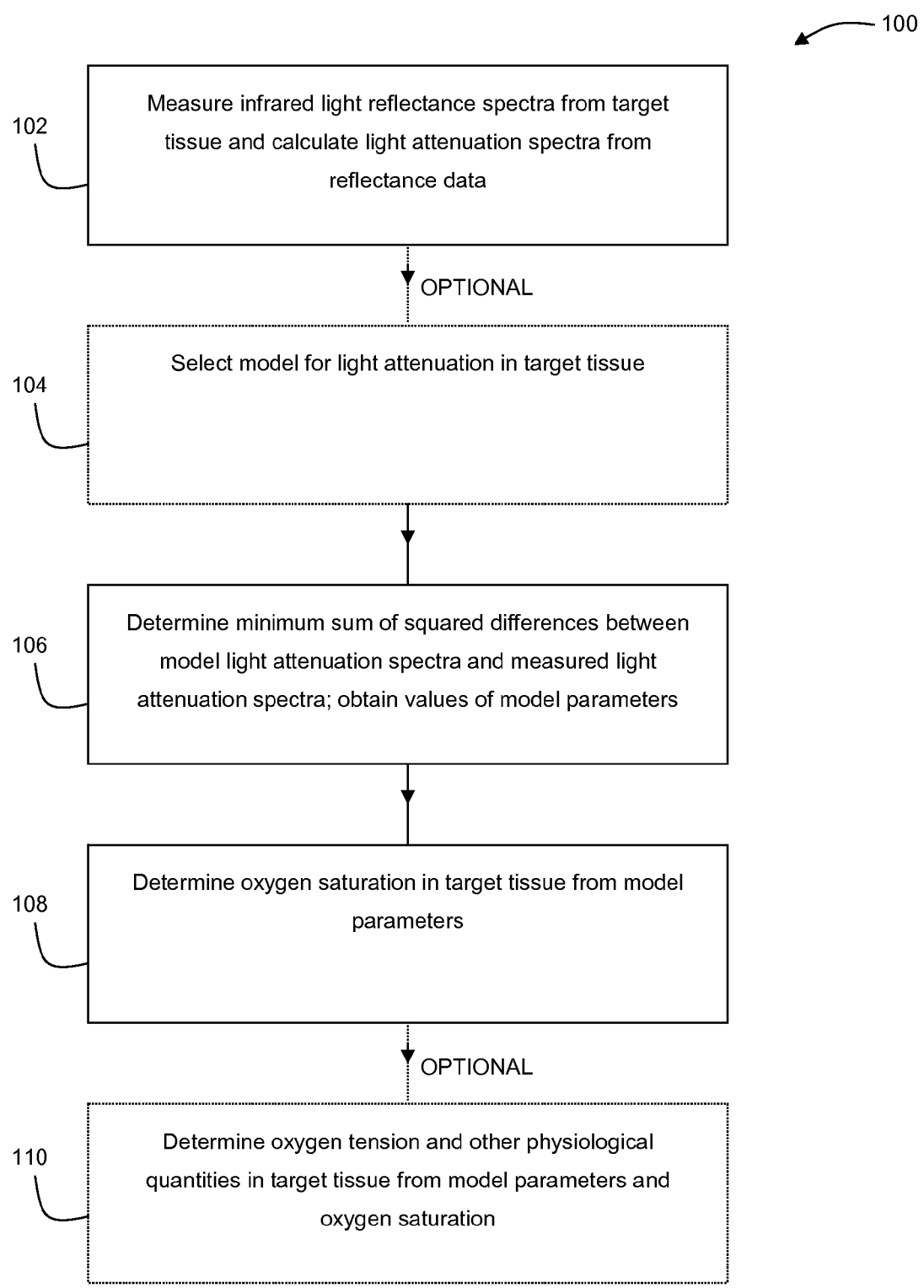
FIG. 3 is a flow chart showing an exemplary series of steps for determining oxygen saturation in a target tissue from light attenuation spectra for the target tissue.

FIG. 3 is a flow chart 100 that shows a series of steps for calculating oxygen saturation in a target tissue from light attenuation spectra, $A_{exp}(\lambda)$, for the target tissue. In a first step 102, one or more light reflectance spectra are collected from a target tissue, and light attenuation spectra are calculated via Equation (3).

In optional step 104, a model $A_{model}(\lambda)$ can be selected to describe light attenuation in the target tissue. In some embodiments, for example, the model selected accounts for both light absorption and light scattering in the target tissue. In certain embodiments, the model includes terms that correspond to one or more of oxygenated hemoglobin and myoglobin, deoxygenated hemoglobin and myoglobin, water, and other species present in the target tissue. A suitable model that can be selected is given by Equation (2), for example. In general, the systems disclosed herein can include one or more models for describing light attenuation in the target tissue. In some embodiments, the systems include only a single model. In certain embodiments, the systems include multiple models, and selection of a model $A_{model}(\lambda)$ can be based on input from a human operator, for example.

In step 106, the model selected in step 104 is used to determine calculated values of light attenuation in the target tissue, and various model parameters are adjusted to minimize a sum of squared differences between the calculated values of light attenuation and the measured light attenuation spectra. The sum of squared differences between the calculated values of light attenuation and the measured light attenuation spectra, $\chi^2$, can be written as $$\chi^2 = \sum_{\lambda_i=\lambda_{min}}^{\lambda_i=\lambda_{max}} [A_{model}(\lambda_i) - A_{exp}(\lambda_i)]^2 \quad (4)$$

where the light attenuation spectra are measured (and theoretical light attenuation values calculated) at a series of wavelengths $\lambda_i$ between $\lambda_{min}$ and $\lambda_{max}$. The value of $\chi^2$ is minimized to yield values of certain adjustable parameters in $A_{model}(\lambda)$. For example, if the model given by Equation (2) is selected, the function $\chi^2$ is minimized to yield values of parameters $c_0$, $c_1$, $c_{Hb+Mb}$, $c_{HbO2+MbO2}$, $c_{wat}$, and <L>.

To obtain accurate values of the model parameters, a non-linear least squares fitting algorithm is used to minimize $\chi^2$ in Equation (4). In some embodiments, fitting constraints on certain model parameters can also be used to improve the accuracy of the parameter values that are obtained. For example, shorter wavelength light typically scatters more efficiently from tissue structures than longer wavelength light, and a wavelength-dependent scattering efficiency curve can therefore be described by a linear functional form with a non-positive slope. A reduced scattering coefficient for the tissue structures, $\mu_s'$, can generally be described by a function such as $$\mu_s' = a + b\lambda \quad (5)$$

where a and b are constants, with $b \leq 0$. Typically, the portions of the measured light attenuation spectra that are due to oxygenated hemoglobin have a positive slope in the infrared region of the spectrum. Thus, when the model given by Equation (2) is selected, parameter $c_1$ can be constrained during fitting so that $c_1 \leq 0$. This constraint enables improved parameter value determination by eliminating cross-talk between contributions to the light attenuation spectra from oxygenated heme, scattering, and a relatively smooth background.

For certain tissues, it may be possible to make good initial estimates for the values of parameters $c_{Hb+Mb}$, $c_{HbO2+MbO2}$, and $c_{wat}$ (e.g., in healthy human patients). For other tissues, it may be more difficult to arrive at good initial estimates for these parameters. Making initial estimates of parameter values typically involves operator intervention, however, and is subject to variability that arises due to differences in skill levels of human operators. Typically, for example, in healthy human patients, the value of $c_{Hb+Mb}$ can be about 40 μmol/L, the value of $c_{HbO2+MbO2}$ can be about 60 μmol/L, and the value of $c_{wat}$ can be about 60%. These values can be used as initial estimates for the parameters $c_{Hb+Mb}$, $c_{HbO2+MbO2}$, and $c_{wat}$.

As an alternative to relying on input from a human operator, the systems and methods disclosed herein can also determine both initial values and final values of model parameters in automated fashion (e.g., without operator input) using a two-stage fitting procedure. The two-stage fitting procedure can, in general, be applied to any of the models disclosed herein to automatically determine good initial values of some or all of the model parameters, and then to determine final parameter values by minimizing the value of $\chi^2$ in Equation (4).

As an example, when the model given by Equation (2) is selected in step 104, good initial values of $c_0$, $c_1$, and $<L>$ can be determined using a sweep method by fixing the values of the parameters $c_{Hb+Mb}$, $c_{HbO2+MbO2}$, and $c_{wat}$, and using a least-squares minimization procedure to vary the values of parameters $c_0$, $c_1$, and $<L>$. This technique corresponds to minimizing the value of $\chi^2$ in Equation (4) with only $c_0$, $c_1$, and $<L>$ as adjustable parameters. When good initial values of $c_0$, $c_1$, and $<L>$ have been determined via minimization of $\chi^2$, these values are fixed and the value of $\chi^2$ in Equation (4) is again minimized via the sweep method by allowing parameters $c_{Hb+Mb}$, $c_{HbO2+MbO2}$, and $c_{wat}$ to vary. The values for these parameters obtained from the minimization procedure correspond to good initial values.

The second stage of the two-stage fitting procedure includes minimizing the value of $\chi^2$ in Equation (4) with each of the six parameters $c_0$, $c_1$, $<L>$, $c_{Hb+Mb}$, $c_{HbO2+MbO2}$, and $c_{wat}$ allowed to vary (subject to any fitting constraints imposed, as discussed previously), and starting from the good initial values of these six parameters determined in the first stage of the procedure. The values of these parameters obtained after the second stage of the procedure are the final values of the parameters. In general, any fitting algorithm that is capable of minimizing the value of $\chi^2$ in Equation (4) subject to any applied constraints can be used in the systems and methods disclosed herein. One example of a fitting algorithm that can be used to minimize value of $\chi^2$ in Equation (4) is the Levenberg-Marquardt algorithm.

The two-stage fitting procedure discussed above can provide a number of advantages. In particular, by initiating the second stage of the fitting procedure with good initial values of the parameters, the second stage proceeds more rapidly to convergence than it would otherwise. Also, fitting results are typically more accurate, because the nonlinear least-squares fitting algorithm is less likely to get stuck in a local (but not necessarily global) minimum.

One algorithm that can be used to fit light attenuation spectra to a selected light attenuation model in the disclosed systems and methods is a type of genetic algorithm called the Differential Evolution (DE) method, which is described in Price, K. V., "Differential Evolution: A practical approach to global optimization," (Germany: Springer-Verlag, 2005). The DE algorithm is a global optimization algorithm that converges to an extreme value of a function irrespective of its initial population. The DE algorithm typically converges faster and uses fewer control variables than other global optimization algorithms. Because the DE algorithm converges to a global minimum, the DE algorithm can be used, in some embodiments, without performing the first stage of the fitting procedure discussed above. That is, a one-stage fitting procedure in which the DE algorithm is used to fit light attenuation spectra to a light attenuation model without first fitting the spectra via the sweep method to determine initial estimates of model parameters can be used.

When final values of the model parameters have been determined, oxygen saturation in the target tissue is calculated in step 108. Oxygen saturation is calculated according to Equation (1); therefore, the model selected in step 104 includes parameters $c_{Hb+Mb}$ and $c_{HbO2+MbO2}$. Values of these parameters are determined in step 106, and then $SO_2$ is calculated from the values of these parameters in step 108.

Determination of Oxygen Tension

In step 110, which is optional in flow chart 100, oxygen tension in the target tissue is calculated from the value of oxygen saturation determined in step 108. Oxygen tension can be calculated from oxygen saturation using a variety of algorithms. For example, oxygen tension can be calculated using the following relationship, which is described in Severinghaus, J. W., "Simple, accurate equations for human blood $O_2$ dissociation computations," *J. Appl. Physiol.: Respirat. Environ. Exercise Physiol.*, 46:599-602 (1979):

$$PO_2 = \exp\left[0.385 \cdot \ln(SO_2^{-1} - 1)^{-1} + 3.32 - (72 \cdot SO_2)^{-1} - \frac{SO_2^6}{6}\right] \quad (6)$$

Equation (6) permits straightforward calculation of oxygen tension from oxygen saturation under standard physiological conditions in step 110 of flow chart 100.

Applications

Oxygen saturation and/or oxygen tension, measured via the systems and methods disclosed herein, provide a sensitive diagnostic indicator of capillary vasoconstriction in patients. Early in the process of hemorrhage and internal bleeding, capillaries in muscle tissues vasoconstrict to direct blood to the heart and brain where it is most needed. Vasoconstriction also helps to maintain blood pressure at relatively normal levels; as a result, blood pressure typically provides only a late-stage indicator of hemorrhagic shock.

To evaluate the sensitivity of the systems and methods disclosed herein, a set of ten test subjects underwent a test protocol that included progressively increasing magnitudes of lower body negative pressure (LBNP). The LBNP protocol consisted of a five minute baseline period, followed by five minute intervals of chamber decompression to −15, −30, −45, and −60 mm Hg, followed by additional increments of −10 mm Hg every five minutes until either the onset of cardiovascular collapse, or the completion of five minutes at −100 mm Hg. Infrared reflectance spectra were recorded continuously throughout the protocol using a fiber optic sensor with both short-distance and long-distance source-detector spacings. The sensor was placed on the flexor digitorum profundus muscle of the forearm.

Oxygen saturation and oxygen tension in the muscle tissue were calculated from light attenuation spectra generated from the reflectance spectra using the methods disclosed above. The reflectance spectra were corrected to remove contributions from light absorption and/or scattering by skin pigments and fat prior to generating the light attenuation spectra. A blood sample was withdrawn from each test subject in the last minute of each stage of the LBNP protocol. Oxygen saturation for each subject was measured from the blood sample using a co-oximeter instrument, and oxygen tension was measured using a blood gas analyzer.

In addition, for each subject at each level of the LBNP protocol, changes in stroke volume (SV), total peripheral resistance (TPR), and total hemoglobin (HbT)—the sum of oxygenated and deoxygenated hemoglobin and myoglobin in the muscle tissue—were determined relative to baseline values of these parameters. Beat-to-beat stroke volume was measured non-invasively using thoracic electrical bioimpedance with an HIC-2000 Bio-Electric Impedance Cardiograph (available from Bio-Impedance Technology, Chapel Hill, N.C.). The thoracic electrical bioimpedance technique is based on the resistance changes in the thorax to a low intensity (e.g., 4 mA), high frequency (e.g., 70 kHz) alternating current applied to the thorax by two outer-surface electrodes placed at the xiphoid process at the midaxillary line. Ventricular SV (in units of mL/beat) was determined from the partly empirical formula $$SV = p \cdot \left(\frac{f}{Z_0}\right)^{-2} \cdot LVET \cdot \left(\frac{dZ}{dt}\right)_{min} \quad (7)$$

where p (in units of ohm-cm) is the blood resistivity (typically about 135 ohm-cm), f (in units of cm) is a mean distance between two inner pick-up electrodes, $Z_0$ (in units of ohms) is a mean baseline thoracic impedance, LVET (in units of seconds) is a left ventricular ejection time, and $(dZ/dt)_{min}$ is a height of a measured thoracic impedance vs. time peak (e.g., a Z-point) from a zero line. Cardiac output (Q) was calculated as the product of heart rate (HR) and SV, and TPR was estimated by dividing a mean value of arterial pressure by Q.

Figure 4:
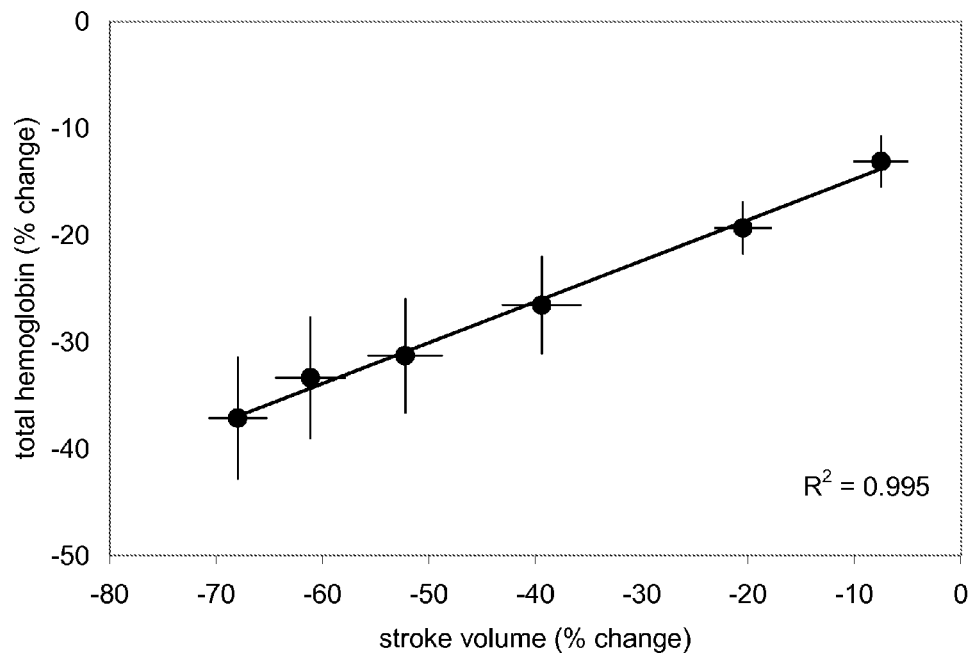
FIG. 4 is a plot showing measured percent change in total hemoglobin as a function of measured percent change in stroke volume for a patient undergoing a lower body negative pressure test protocol.
Figure 5:
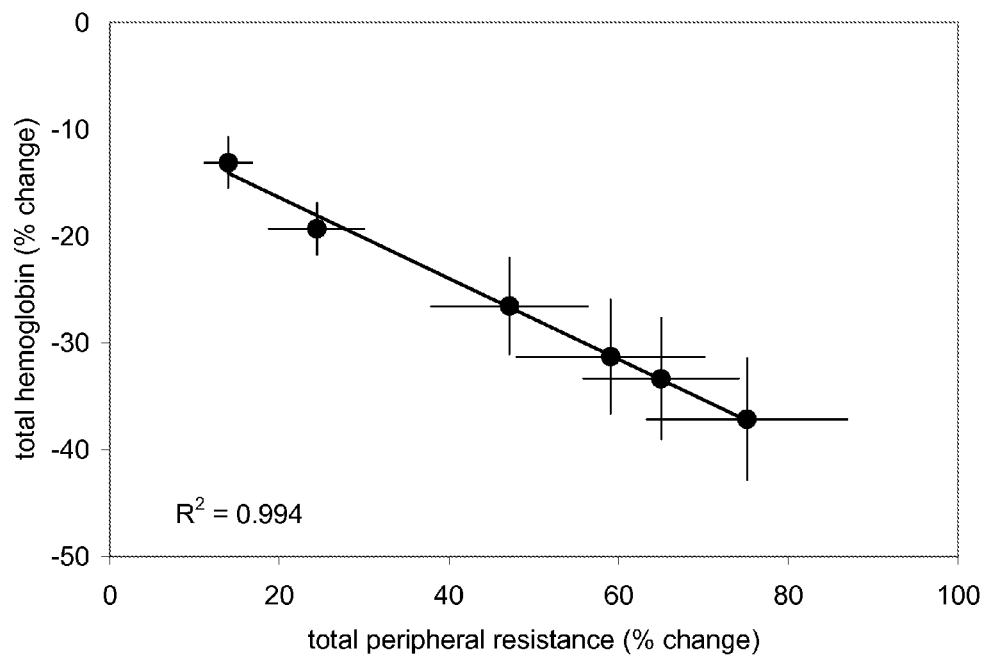
FIG. 5 is a plot showing measured percent change in total hemoglobin as a function of measured percent change in total peripheral resistance for a patient undergoing a lower body negative pressure test protocol.

FIG. 4 shows the measured percent change in total hemoglobin as a function of the measured percent change in stroke volume. The relationship between the changes in total hemoglobin and stroke volume is approximately linear, as indicated by the solid line in FIG. 4. Without wishing to be bound by theory, one possible explanation for the relationship shown in FIG. 4 is that stroke volume falls as blood volume decreases. In FIG. 5, the percent change in total hemoglobin is plotted as a function of the percent change in total peripheral resistance. The relationship is again approximately linear as shown by the solid line. However, FIG. 5 shows that changes in total hemoglobin are inversely correlated with changes in total peripheral resistance. Typically, total peripheral resistance increases when vasoconstriction occurs. Thus, measurement of total hemoglobin in muscle tissue (by determining concentrations of oxygenated and deoxygenated hemoglobin, as discussed above) provides an accurate diagnostic for the onset and progression of vasoconstriction in patients.

More generally, vasoconstriction and/or vasodilation produce changes in blood volume in a target tissue, and by monitoring total hemoglobin, blood volume in the tissue (e.g., changes in blood volume over time in a patient) can be assessed. Values of $SO_2$ and $PO_2$ determined via the methods disclosed herein also provide sensitive probes of blood volume in a target tissue, and can be used for monitoring and assessment purposes. In general, measurements of quantities such as HbT, $SO_2$, and $PO_2$ are useful for tracking progression and treatment of any disease or condition that results in variation of blood volume in tissues, and/or vasoconstriction/vasodilation in response to an insult. Examples of conditions for which progression can be tracked include: diagnosis of, and evaluation of treatment for, hemorrhage and sepsis; microvascular abnormalities that accompany heart disease and diabetes; and effects of drugs that raise blood pressure through vasoconstriction and/or vasodilation. In animal patients, regional effects of drugs on specific organs can be tracked.

As an example, when a patient undergoes hemorrhaging, the loss of blood volume in certain patient tissues can be monitored by measuring total hemoglobin. Further, as shown in FIGS. 4 and 5, total hemoglobin scales linearly with blood volume. Therefore, by monitoring HbT over time, a stage of progress of a hemorrhage can be assessed. Changes in HbT can be used to assess whether a hemorrhage has been halted or is under control, for example, or whether the hemorrhaging condition is worsening.

As another example, when a patient suffers from sepsis—a microcirculatory disease—small blood vessels in certain tissues of the patient become clogged, resulting in a smaller blood volume (and oxygen-depleted blood) being present in the patient's tissues. Generally, as sepsis persists, the level of oxygen-depletion in blood tissue increases. If perfusion is restored, the sepsis condition is alleviated, and both blood oxygenation and blood volume increase in the patient's tissues. By monitoring HbT and/or $SO_2$ and/or $PO_2$ in patient tissues, as disclosed herein, the rate of progress of sepsis can be assessed. For example, when a sepsis condition in a target tissue is worsening, the value of HbT in the tissue decreases with decreasing blood volume. As sepsis in the tissue is alleviated, the value of HbT in the tissue increases with increasing blood volume. Similar correlations apply to assessing sepsis based on blood volume determined from measurements of $SO_2$ and $PO_2$ in the target tissue.

As a third example, when a patient suffers from heart disease or diabetes, atherosclerosis which results from these conditions prevents vasoconstriction in response to a challenge. In contrast, in a healthy patient, vasoconstriction in response to a challenge occurs to maintain blood pressure. Thus, progress of a condition such as heart disease or diabetes can be assessed by monitoring HbT and/or $SO_2$ and/or $PO_2$ in the patient. Typically, for example, a patient suffering from one of these conditions is either tilted or subjected to an exercise protocol which represents a challenge, and values of $SO_2$ and/or $PO_2$ and/or and HbT are determined from a selected target tissue of the patient. Due to the inability of the patient's blood vessels to vasoconstrict, measured changes in $SO_2$ and/or $PO_2$ and/or and HbT for the patient will be smaller than the measured changes in these parameters would be for a healthier patient. By measuring the difference in the values of $SO_2$ and/or $PO_2$ and/or and HbT for the afflicted patient's tissue relative to standard values for a healthy patient's tissue (or relative to values of these parameters measured from the same patient at an earlier stage of the disease), the progress of conditions such as heart disease and diabetes can be assessed.

In general, as discussed above, measurements of quantities such as HbT, $SO_2$, and $PO_2$ for assessment and tracking of various conditions are performed during interventions that stimulate vasoconstriction to maintain blood pressure and/or vasodilation to improve blood flow. Examples of such interventions include occluding one or more blood vessels, exercising a subject, and tilting a subject.

Implementation

The equations and algorithms disclosed herein can be implemented in hardware or in software, or in a combination of both. The method steps and figures disclosed herein can be implemented in computer programs using standard programming techniques. The programs can be designed to execute on programmable processors (such as processor 18) or computers, e.g., microcomputers, each including at least one processor, at least one data storage system (including volatile and non-volatile memory and/or storage elements), at least one input device, such as a keyboard or push button array, and at least one output device, such as a CRT, LCD, or printer. Program code is applied to input data to perform the functions described herein. The output information is applied to one or more output devices such as a printer, or a CRT or other monitor, or a web page on a computer monitor with access to a website, e.g., for remote monitoring.

Each program used in the systems disclosed herein is preferably implemented in a high level procedural or object oriented programming language to communicate with a computer system. However, the programs can be implemented in assembly or machine language, if desired. In any case, the language can be a compiled or interpreted language.

Each such computer program can be stored on a storage medium or device (e.g., ROM or magnetic diskette) readable by a general or special purpose programmable computer, for configuring and operating the computer when the storage medium or device is read by the computer to perform the procedures described herein. The programs can also be considered to be implemented as a computer-readable storage medium, configured with a computer program, where the storage medium so configured causes a processor in the computer to operate in a specific and predefined manner to perform the functions described herein.

Although any communications network can be used to obtain results from remote monitoring, the Internet or wireless systems provide useful choices to transmit data.

EXAMPLES

The invention is further described in the following examples, which are not intended to limit the scope of the invention described in the claims.

Example 1

To evaluate the accuracy of the systems and methods disclosed herein, simulated tissue attenuation spectra were calculated for four different light scattering conditions in a target tissue, and the method steps of FIG. 3 were applied to the data from each of the four light scattering conditions to determine values of oxygen saturation. The four light scattering conditions correspond to four different target tissues of interest. For each target tissue, simulated light attenuation spectra were calculated for each of eight different theoretical $SO_2$ values: 0%, 10%, 20%, 40%, 50%, 60%, 80%, and 100%.

To generate light attenuation spectra that corresponded to a non-scattering, absorbing target tissue, a Lambert-Beer equation with terms that correspond only to contributions from hemoglobin was used:

$$A_{exp}(\lambda) = \ln(10) \cdot L \cdot [c_{Hb}\epsilon_{Hb} + c_{HbO2}\epsilon_{HbO2} + c_{wat}\epsilon_{wat}] \quad (8)$$

where L is a path length of the attenuated light through the target tissue, $c_{Hb}$, $c_{HbO2}$, and $c_{wat}$ are concentrations of deoxygenated hemoglobin, oxygenated hemoglobin, and water in the target tissue, respectively, and $\epsilon_{Hb}(\lambda)$, $\epsilon_{HbO2}(\lambda)$, and $c_{wat}(\lambda)$ are extinction coefficients of deoxygenated hemoglobin, oxygenated hemoglobin, and water as a function of the wavelength $\lambda$. Values of these parameters were selected to generate light attenuation spectra for a non-scattering, absorbing target tissue.

Light attenuation spectra were also calculated for three different target tissues in which light scattering occurred. A single layer infinite slab diffusion model was used to generate light attenuation spectra for selected values of a tissue absorption coefficient $\mu_a(\lambda)$, a reduced scattering coefficient $\mu_s'(\lambda)$, and a source-probe spacing d, from a model with the functional form $$A_{exp}(\lambda) = -\ln\left[\frac{\sinh\left(\frac{\sigma(\lambda)}{\mu_s'(\lambda)}\right)}{\sqrt{2\pi}\sinh(\sigma(\lambda) \cdot d)}\right] \quad (9)$$

where the quantity $\sigma(\lambda)$ is calculated according to $$\sigma(\lambda) = \sqrt{3\mu_a(\lambda) \cdot [\mu_a(\lambda) + \mu_s'(\lambda)]} \quad (10)$$

To calculate the light attenuation spectra for the three different light scattering target tissues, values for the concentrations of oxygenated and deoxygenated hemoglobin were selected to fix the theoretical values of $SO_2$, and values for the absorption coefficient $\mu_a(\lambda)$ were selected. In addition, values of the reduced light scattering coefficient $\mu_s'(\lambda)$ for each of the light scattering target tissues were selected. The three different light scattering target tissues corresponded to tissues in a forearm, a calf, and an intact head of a patient. The reduced scattering coefficients $\mu_s'(\lambda)$ for each of these tissues were calculated according to Equations (11), (12), and (13), respectively:

$$\mu_s'(\lambda) = -\frac{5.1 \cdot \lambda}{1000} + 11 \quad (11)$$

$$\mu_s'(\lambda) = -\frac{8.9 \cdot \lambda}{1000} + 16.3 \quad (12)$$

$$\mu_s'(\lambda) = -\frac{6.5 \cdot \lambda}{1000} + 14.5 \quad (13)$$

Equations (11)-(13) are described in Matcher, S. J. et al., "In vivo measurements of the wavelength dependence of tissue-scattering coefficients between 760 and 900 nm measured with time-resolved spectroscopy," *Applied Optics*, 36:386-396 (1997). In Equations (11)-(13), $\mu_s'(\lambda)$ is in units of $cm^{-1}$ and $\lambda$ is in units of nm. Light attenuation spectra for the three different target tissues corresponding to Equations (11)-(13) were calculated at a series of wavelength points between 725 nm and 880 nm.

To assess the accuracy of values of $SO_2$ determined by fitting the calculated light attenuation data to a light attenuation model, a coefficient of determination $R^2$ between the measured and theoretical values of $SO_2$ for each tissue was calculated. In addition, values of the root-mean-square error of prediction (RMSEP), which describes the estimated measurement error, were calculated according to $$RMSEP = \sqrt{\frac{\sum_{i=1}^{N}(\hat{y}_i - y_i)^2}{N}} \quad (14)$$

where N is the number of light attenuation spectra, and $\hat{y}_i$ and $y_i$ are theoretical and experimentally determined values of $SO_2$, respectively. Relatively large values of $R^2$ (e.g., values approaching unity) and relatively small values of RMSEP indicate that the experimentally determined $SO_2$ values are accurate (e.g., match the theoretical $SO_2$ values closely).

Figure 6:
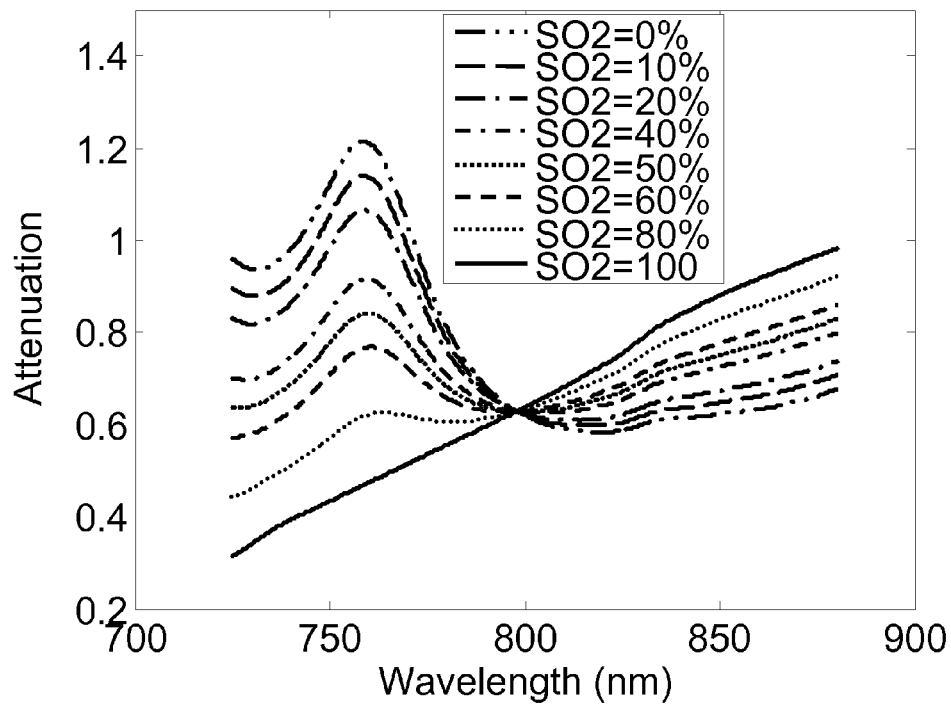
FIG. 6 is a plot showing theoretical light attenuation spectra calculated for a non-scattering target tissue at a series of different tissue oxygen saturation values.
Figure 7:
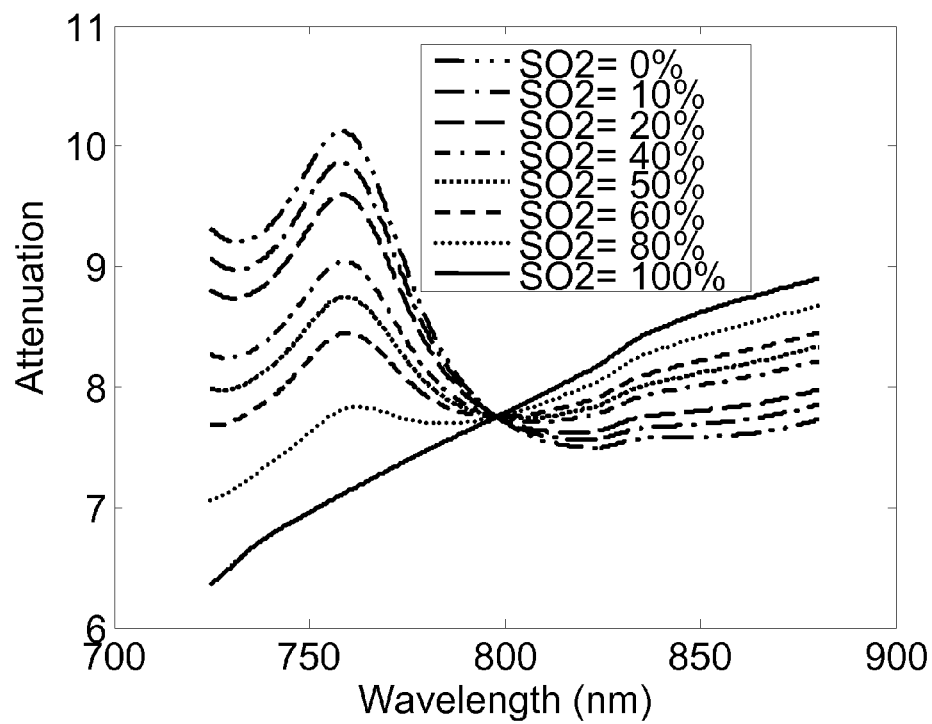
FIG. 7 is a plot showing theoretical light attenuation spectra calculated for a scattering target tissue at a series of different tissue oxygen saturation values.

Simulated light attenuation spectra calculated using Equation (8) are shown in FIG. 6 for a series of theoretical values of $SO_2$. The light attenuation spectra in FIG. 6 correspond to a target tissue that does not scatter incident light (e.g., light attenuation occurs by absorption only). Simulated light attenuation spectra calculated for a light scattering target tissue that corresponds to a forearm of a patient are shown in FIG. 7 for a series of theoretical values of $SO_2$. In each of FIGS. 6 and 7, a water concentration $c_{wat}$ of 60% and a source-detector spacing d of 3 cm were used in the calculations.

Figure 8:
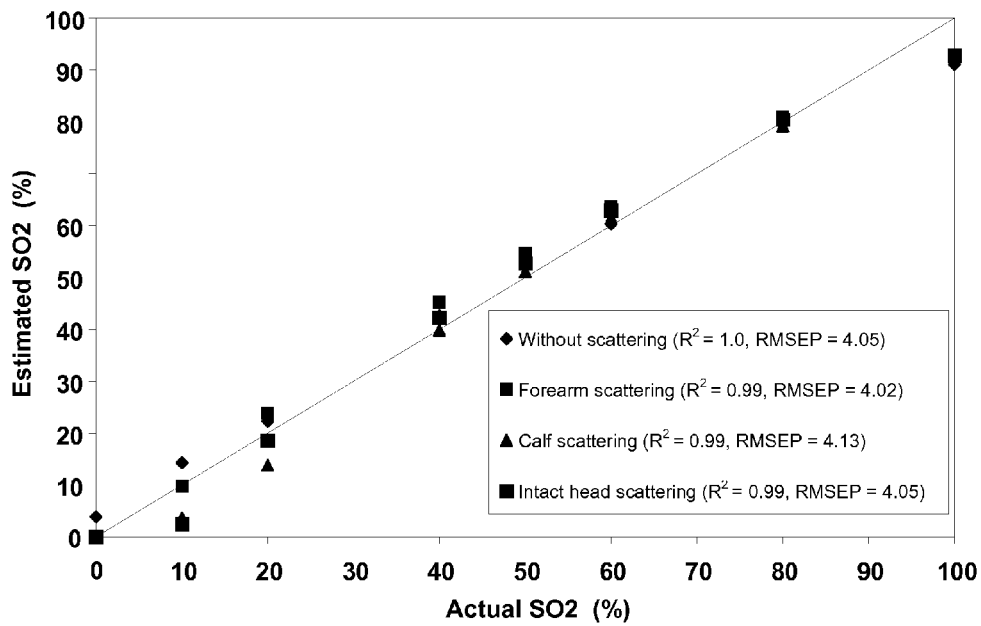
FIG. 8 is a plot comparing actual and estimated values of oxygen saturation in different target tissues.

FIG. 8 is a plot showing actual (theoretical) and estimated (measured) values of $SO_2$, determined by fitting the four sets of light attenuation spectra calculated using Equations (8)-(13) to the model given by Equation (2) according to the procedure shown in FIG. 3. The fitting algorithm used was a Levenberg-Marquardt optimization method with initial parameter values obtained from the sweep technique discussed above. Values of $R^2$ between 0.99 and 1 were obtained for each of the four sets of attenuation spectra (e.g., for each of the four different target tissues), with a maximum RMSEP of less than 5% $SO_2$. The relatively high values of $R^2$ and relatively low RMSEP values indicate that accurate measurements of $SO_2$ in each of the four target tissues were achieved. For comparison, the theoretical light attenuation spectra were also fitted to Equation (2) using a DE algorithm, and the values of the model parameters obtained from the fitting procedure were used to calculate $SO_2$ values. The results are shown in Table 1 below. For three of the four target tissues, the RMSEP for $SO_2$ determined via the DE algorithm was lower than the RMSEP for $SO_2$ determined via the Levenberg-Marquardt algorithm.

TABLE 1

| Target Tissue Type | $R^2$ | RMSEP (% $SO_2$) |
|---|---|---|
| Non-scattering | 0.99 | 1.31 |
| Forearm scattering | 0.99 | 4.10 |
| Calf scattering | 0.99 | 3.86 |
| Intact Head scattering | 0.99 | 2.81 |

Example 2

To simulate the early stages of hemorrhagic shock in human patients, a test protocol that included progressively increasing magnitudes of lower body negative pressure (LNBP) in five human test subjects was performed. The LBNP protocol consisted of a five minute baseline period, followed by five minute intervals of chamber decompression to −15, −30, −45, and −60 mm Hg, followed by additional increments of −10 mm Hg every five minutes until either the onset of cardiovascular collapse, or the completion of five minutes at −100 mm Hg. Infrared reflectance spectra were recorded continuously throughout the protocol using a fiber optic sensor with both short-distance and long-distance source-detector spacings. The sensor was placed on the flexor digitorum profundus muscle of the forearm.

Oxygen saturation and oxygen tension in the muscle tissue were calculated from light attenuation spectra generated from the reflectance spectra using the methods disclosed above. The reflectance spectra were corrected to remove contributions from light absorption and/or scattering by skin pigments and fat prior to generating the light attenuation spectra. A blood sample was withdrawn from each test subject in the last minute of each stage of the LBNP protocol. Oxygen saturation for each subject was measured from the blood sample using a co-oximeter instrument, and oxygen tension was measured using a blood gas analyzer.

Figure 9:
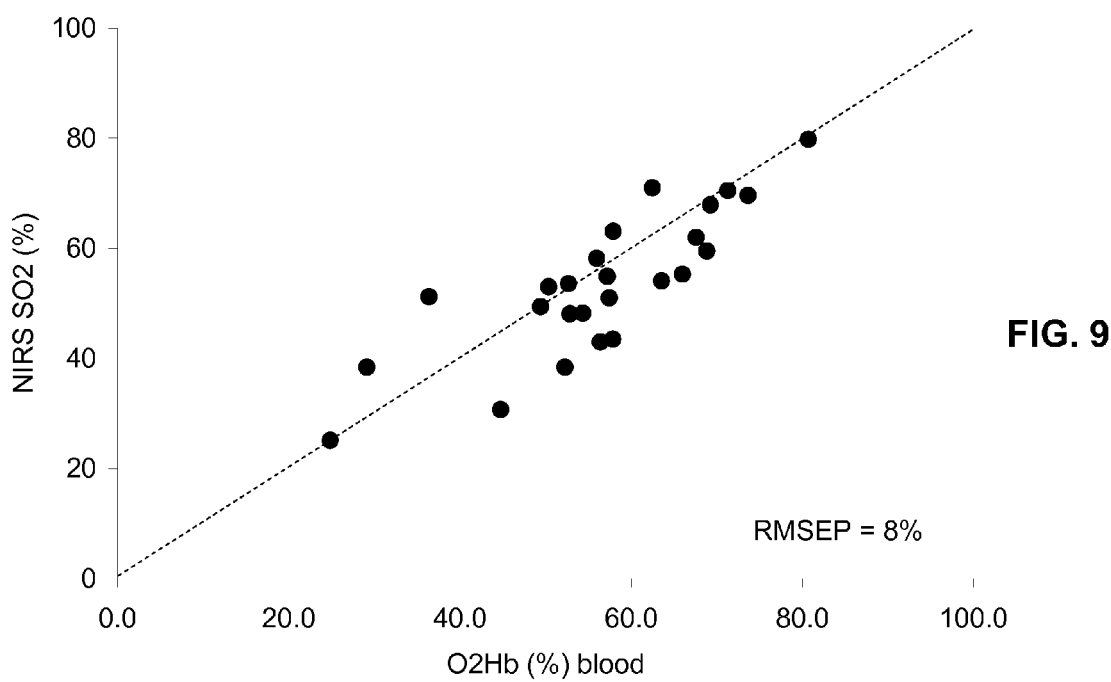
FIG. 9 is a plot comparing oxygen saturation values measured from withdrawn blood samples and from non-invasive infrared reflectance measurements for patients at various stages of a lower body negative pressure test protocol.
Figure 10:
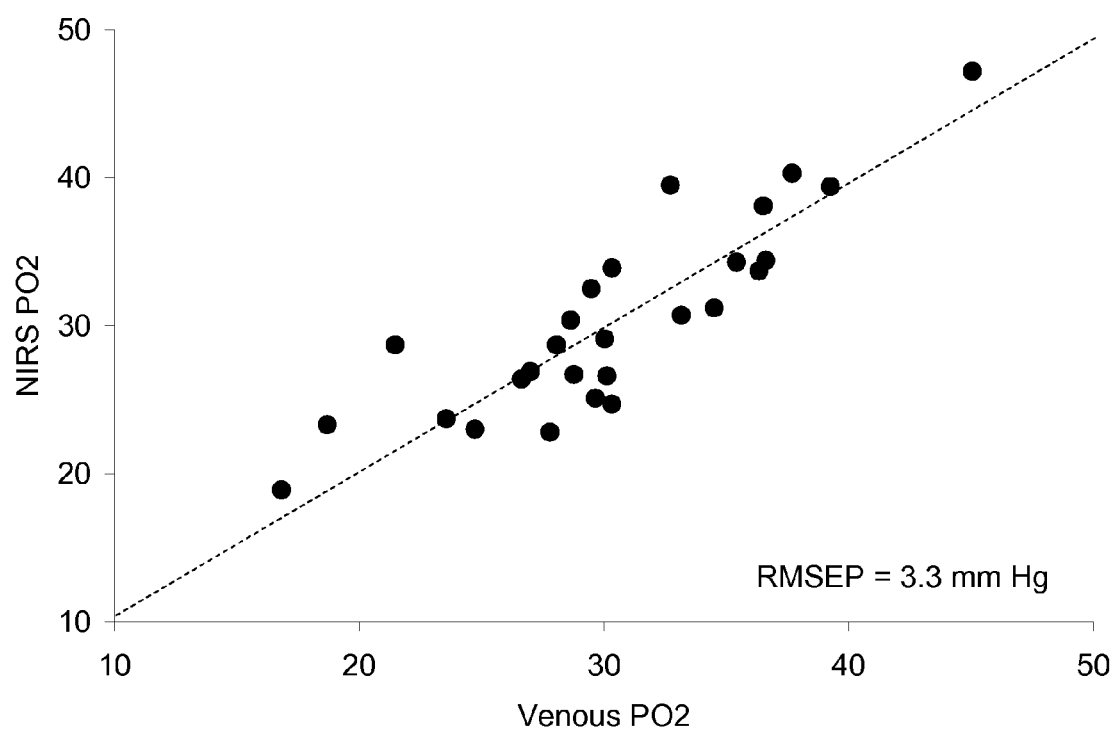
FIG. 10 is a plot comparing oxygen tension values measured from withdrawn blood samples and from non-invasive infrared reflectance measurements for patients at various stages of a lower body negative pressure test protocol.

FIG. 9 shows the correlation between oxygen saturation measured from withdrawn blood samples (O2Hb (%) blood) and oxygen saturation measured via infrared reflectance measurements (NIRS SO2(%)) at various stages of the LNBP protocol for each of the five test subjects. FIG. 10 shows the correlation between oxygen tension measured from withdrawn blood samples (Venous $PO_2$) and oxygen tension measured via infrared reflectance measurements (NIRS $PO_2$) during the LNBP protocol for each of the five subjects. In FIG. 9, the RMSEP in $SO_2$ is about 8%, and in FIG. 10, the RMSEP in $PO_2$ is about 3.3 mm Hg. These relatively low errors of prediction indicate that $SO_2$ and $PO_2$ values determined via infrared reflectance measurements correspond accurately to actual $SO_2$ and $PO_2$ values in target tissues. The accuracy of the $SO_2$ and $PO_2$ values further indicates that the systems and methods disclosed herein provide accurate and sensitive diagnosis of conditions such as hemorrhagic shock in patients.

Other Embodiments

The systems and methods disclosed herein can make use of other light attenuation models (e.g., models other than Equation (2)) to determine $SO_2$ and other physiological quantities such as $PO_2$ in target tissues. Three different alternative models will be discussed; other models are also possible. The following alternative models have been investigated for accuracy by fitting sets of theoretical light attenuation spectra generated using Equations (8)-(13), and corresponding to four different target tissues (e.g., non-scattering tissue, forearm tissue, calf tissue, and intact head tissue), to each of the models, and calculating coefficients of determination and RMSEP values for values of $SO_2$ determined for each target tissue using each model.

Model 2

As discussed above, measured light attenuation spectra can be fitted to the model given by Equation (2). Following the fitting procedure, values of the parameters $c_0$, $c_1$, $\langle L \rangle$, $c_{Hb+Mb}$, $c_{HbO2+MbO2}$, and $c_{wat}$ are obtained. Using the values of these parameters, a wavelength-dependent baseline spectrum is calculated from a difference between the model given by Equation (2) with fitted values of the parameters, and the measured light attenuation spectra. The baseline spectrum is calculated according to $$bspect(\lambda) = \hat{A}_{exp}(\lambda) - A_{exp}(\lambda) \quad (15)$$

where $\hat{A}_{exp}(\lambda)$ is the light attenuation model function given by Equation (2) with the best-fit parameter values.

Then in a subsequent step, with fitted values of the parameters $c_0$, $c_1$, $\langle L \rangle$, $c_{Hb+Mb}$, $c_{HbO2+MbO2}$, and $c_{wat}$ as initial parameter values, the measured light attenuation spectra are fitted to the model equation $$A_{model}(\lambda) = c_2[bspect(\lambda) + c_0 + c_1\lambda] + \ln(10) \cdot \quad (16)$$
$$\langle L \rangle \cdot [c_{Hb+Mb}\varepsilon_{Hb}(\lambda) + c_{HbO2+MbO2}\varepsilon_{HbO2+MbO2}(\lambda) + c_{wat}\varepsilon_{wat}(\lambda)]$$

In the model given by Equation (16), $c_2$ is a scale factor that is varied along with the other fitting parameters. From refined values of $c_{Hb+Mb}$ and $c_{HbO2+MbO2}$ that are obtained by fitting Equation (16) to the measured light attenuation spectra, values of $SO_2$ and $PO_2$ are calculated.

This multi-step fitting procedure—first, to determine baseline spectrum $bspect(\lambda)$, and second, to determine $SO_2$ and $PO_2$ from fitted values of the parameters in Equation (16)—provides for more accurate determination of the parameters in Equation (16), and therefore, more accurate $SO_2$ and $PO_2$ values. Table 2 below shows $R^2$ and RMSEP values calculated for each of the four different theoretical target tissues for which light attenuation spectra were simulated using Equations (8)-(13). Values of $SO_2$ determined from fitting the theoretical light attenuation spectra using the multi-step fitting procedure discussed above were compared to the theoretical values of $SO_2$, which yielded an $R^2$ value of 0.99 for each of the tissues, and RMSEP values of less than 6% $SO_2$. The relatively large $R^2$ values and relatively low RMSEP values indicated that Model 2 provided accurate determination of $SO_2$ in target tissues.

TABLE 2

| Target Tissue Type | $R^2$ | RMSEP (% $SO_2$) |
| --- | --- | --- |
| Non-scattering | 0.99 | 1.73 |
| Forearm scattering | 0.99 | 3.69 |
| Calf scattering | 0.99 | 4.66 |
| Intact Head scattering | 0.99 | 5.77 |

Model 3

In this model, light attenuation by absorption and by scattering have similar functional forms. The model equation is $$A_{model}(\lambda) = [\mu_a(\lambda) + \mu_s(\lambda)] \cdot d \cdot dpf(\lambda) \quad (17)$$
$$= [\mu_a(\lambda) + c_1 \cdot \mu_s'(\lambda)] \cdot d \cdot dpf(\lambda)$$

where $\mu_a(\lambda)$ and $\mu_s(\lambda)$ are wavelength-dependent absorption and scattering coefficients of the target tissue, respectively, $c_1$ is a constant, d is a source-detector distance, and dpf($\lambda$) is a differential path length factor for the tissue. The scattering coefficient $\mu_s(\lambda)$ is related to the reduced scattering coefficient $\mu_s'(\lambda)$ according to $\mu_s'(\lambda)=(1-g)\mu_s(\lambda)$, where g is an anisotropy factor that corresponds to an average cosine of the scattering angle.

To compensate for a difference between absolute light intensity $I_0(\lambda)$ and the reference light intensity $I_{ref}(\lambda)$ from a 99% reflectance standard, as discussed above, a constant term $c_0$ can be added to Equation (17) to yield a model equation $$A_{model}(\lambda) = [\mu_a(\lambda) + \mu_s(\lambda)] \cdot L \cdot dpf(\lambda) + c_0 \quad (18)$$
$$= [\mu_a(\lambda) + c_1 \cdot \mu_s'(\lambda)] \cdot L \cdot dpf(\lambda) + c_0$$

In Equation (18), the absorption coefficient $\mu_a(\lambda)$ is related to concentrations of absorbing components in the target tissue according to $$\mu_a(\lambda) = c_{Hb+Mb}\epsilon_{Hb}(\lambda) + c_{HbO2+MbO2}\epsilon_{HbO2}(\lambda) + c_{wat}\epsilon_{wat}(\lambda) \quad (19)$$

The reduced scattering coefficient $\mu_s'(\lambda)$ is a function of two constants, $c_2$ and $c_3$, according to $$\mu_s'(\lambda) = c_2 + c_3\lambda \quad (20)$$

During the fitting procedure, constraints are imposed on $c_3$ so that $c_3 < 0$.

The differential path length factor is expressed as a function of the reduced scattering coefficient and the absorption coefficient according to $$dpf(\lambda) = \frac{\sqrt{3\mu_s'(\lambda)}}{2\sqrt{\mu_a(\lambda)}} \quad (21)$$

A nonlinear Levenberg-Marquardt least-squares fitting procedure was used to determine values of the various model parameters by fitting the theoretical (e.g., simulated) light attenuation spectra to the model given by Equations (18)-(21). Values of $SO_2$ were then calculated from the fitted values of the parameters in Equation (19). Table 3 below shows $R^2$ and RMSEP results from a comparison of experimentally determined $SO_2$ values and theoretical $SO_2$ values. As shown in the table, $R^2$ values were 0.97 or larger for all four target tissues, and RMSEP values were less than 10% $SO_2$. These statistical measures indicate that Model 3 provided for accurate determination of $SO_2$ in the target tissues.

Comparing to the results for Model 2, Model 3 appears to provide slightly less accurate results on average for the test data evaluated herein. However, for certain tissues, Model 3 may provide more accurate $SO_2$ determinations (e.g., compare results for intact head target tissue).

TABLE 3

| Target Tissue Type | $R^2$ | RMSEP (% $SO_2$) |
| --- | --- | --- |
| Non-scattering | 0.99 | 1.81 |
| Forearm scattering | 0.97 | 9.37 |
| Calf scattering | 0.97 | 7.09 |
| Intact Head scattering | 0.99 | 5.18 |

Model 4

Models based on diffusion theory can also be used in the systems and methods disclosed herein. According to diffusion theory, the diffuse reflectance, R(d,$\lambda$), of continuous-wave light radiation emitted from a semi-infinite scattering medium at a source-detector separation d larger than about 2 cm, is given by $$R(d, \lambda) = \frac{I(\lambda)}{I_0(\lambda)} = \frac{1 + \frac{2C}{3}}{2\pi}\left[\mu_{eff}(\lambda) + \frac{1}{d}\right]\frac{e^{-\mu_{eff}(\lambda)d}}{d^2} \quad (22)$$

where C is a constant that is independent of d and related to an internal specular reflection parameter. The value of C depends on the refractive indices of the target tissue and surrounding medium. Values of $\mu_{eff}(\lambda)$ are calculated according to $$\mu_{eff}(\lambda) = \sqrt{3\mu_a(\lambda) \cdot [\mu_a(\lambda) + \mu_s'(\lambda)]} \quad (23)$$

The absorption coefficient $\mu_a(\lambda)$ is calculated as in Equation (19), and the reduced scattering coefficient $\mu_s'(\lambda)$ is calculated as in Equation (20). A constant term $c_0$ is also added to compensate for differences between $I_0(\lambda)$ and $I_{ref}(\lambda)$, as discussed above, so that the model light attenuation equation is $$A_{model}(d, \lambda) = \ln\left(\frac{I_0(\lambda)}{I(\lambda)}\right) = -\ln R(d, \lambda) + c_0 \quad (24)$$

A two-stage nonlinear least-squares fitting procedure was used to determine parameters of the model given by Equations (19), (20), and (22)-(24) by fitting the equations to the theoretical data for each of the four different target tissues. In a first stage of the fitting procedure, prior to performing a fit of all of the model parameters to the data, a good initial value of the parameter C was obtained by using the sweep method. Values of the parameters $c_0$, $c_2$, $c_3$, $c_{Hb+Mb}$, $c_{HbO2+MbO2}$, and $c_{wat}$, were held constant, and the theoretical light attenuation spectra were fitted to Equation (24), allowing only C to vary among the model parameters. Fitting the data to Equation (24) included minimizing a sum of squared differences, $\chi^2$, between the model and the theoretical data, as discussed in connection with Equation (4). The value of C obtained from the sweep method corresponded to a good estimate for parameter C.

In the second stage of the fitting procedure, the value of C determined in the first stage was used as the final value of C in Equation (22) (e.g., fixed as a constant), and the theoretical light attenuation spectra were again fitted to Equation (24), permitting each of the parameters $c_0$, $c_2$, $c_3$, $c_{Hb+Mb}$, $c_{HbO2+MbO2}$, and $c_{wat}$ to vary during fitting. In this manner, accurate values of the six parameters were obtained, and $SO_2$ in each of the target tissues was calculated based on the values of $c_{Hb+Mb}$ and $c_{HbO2+MbO2}$ from the fitting procedure. Table 4 below shows $R^2$ and RMSEP results from a comparison of experimentally determined $SO_2$ values and theoretical $SO_2$ values. As shown in the table, $R^2$ values were 0.99 for all four target tissues, and RMSEP values were less than 7% $SO_2$. These statistical measures indicate that Model 4 provided for accurate determination of $SO_2$ in the four target tissues. Based on the $R^2$ and RMSEP values, the results for each of Models 2, 3, and 4 achieved comparable accuracy.

TABLE 4

| Target Tissue Type | $R^2$ | RMSEP (% $SO_2$) |
| --- | --- | --- |
| Non-scattering | 0.99 | 1.52 |
| Forearm scattering | 0.99 | 5.35 |
| Calf scattering | 0.99 | 6.63 |
| Intact Head scattering | 0.99 | 5.99 |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for calculating oxygen saturation in a target tissue, the method comprising:
    directing incident radiation from a source to a target tissue and determining reflectance spectra of the target tissue with a detector by measuring intensities of reflected radiation from the target tissue at a plurality of radiation wavelengths;
    correcting the measured intensities of the reflectance spectra to reduce contributions thereto from skin and fat layers through which the incident radiation propagates;
    determining oxygen saturation in the target tissue based on the corrected reflectance spectra; and
    outputting the determined value of oxygen saturation,
    wherein determining reflectance spectra of the target tissue comprises:
    measuring, at a first source-detector spacing, a first reflectance spectrum from the target tissue that comprises a first weighting of contributions from the target tissue and from the skin and fat layers, and measuring, at a second source-detector spacing different from the first source-detector spacing, a second reflectance spectrum from the target tissue that comprises a second weighting of contributions from the target tissue and from the skin and fat layers different from the first weighting; and
    wherein correcting the measured intensities of the reflectance spectra comprises:
    correcting the measured intensities of the first reflectance spectrum based on the measured intensities of the second reflectance spectrum.

2. The method of claim 1, wherein determining oxygen saturation comprises determining light attenuation spectra from the corrected reflectance spectra, and calculating oxygen saturation based on concentrations of oxygenated and deoxygenated heme in the target tissue that are derived from the light attenuation spectra, wherein heme comprises hemoglobin and myoglobin in the target tissue.

3. The method of claim 2, wherein the concentrations of oxygenated and deoxygenated heme are derived from the light attenuation spectra by fitting the light attenuation spectra to a model light attenuation equation.

4. The method of claim 3, wherein the light attenuation equation comprises a Beer's Law equation comprising terms that correspond to incident light absorption by oxygenated heme, deoxygenated heme, and water in the target tissue.

5. The method of claim 4, wherein the light attenuation equation comprises a series expansion of light attenuation in a plurality of terms that correspond to Beer's Law absorption terms.

6. The method of claim 5, wherein the series expansion of light attenuation comprises a Taylor series expansion of light attenuation.

7. The method of claim 4, wherein the light attenuation equation further comprises a baseline function derived from a difference between light attenuation values determined from the light attenuation equation and the light attenuation spectra.

8. The method of claim 4, wherein the light attenuation equation further comprises a differential path length factor that varies directly with a scattering coefficient of the target tissue and inversely with an absorption coefficient of the target tissue.

9. The method of claim 3, wherein the light attenuation equation comprises a term that varies linearly with a wavelength of the incident light, the term having a functional form $a\lambda$ where a is a constant and $\lambda$ is the wavelength of the incident light.

10. The method of claim 9, wherein the value of a is constrained during fitting so that a assumes only values that are less than or equal to zero.

11. The method of claim 3, wherein the light attenuation equation comprises a constant term independent of a wavelength of the incident light.

12. The method of claim 3, wherein fitting the light attenuation spectra to a model comprises performing a two-stage fitting procedure wherein, in a first stage, initial values of one or more model parameters are determined, and in a second stage, the light attenuation spectra are fitted to the model, wherein the model comprises the initial parameter values determined in the first stage.

13. The method of claim 12, wherein the light attenuation spectra are fitted to the model by minimizing a sum of squared differences between the light attenuation spectra and light attenuation values determined from the model.

14. The method of claim 3, wherein the fitting is performed automatically by a processor.

15. The method of claim 3, wherein the light attenuation equation comprises a diffuse reflectance equation derived from a radiation diffusion model of incident light in the target tissue.

16. The method of claim 2, further comprising assessing a level of vasoconstriction in a patient based on a measurement of total hemoglobin in a target tissue of the patient, wherein total hemoglobin is determined based on the concentrations of oxygenated and deoxygenated heme in the target tissue.

17. The method of claim 1, wherein correcting the measured intensities of the first reflectance spectrum comprises reducing contributions from the skin and fat layers to the first reflectance spectrum based on the measured intensities of the second reflectance spectrum.

18. The method of claim 1, further comprising determining oxygen tension in the target tissue based on oxygen saturation in the target tissue.

19. The method of claim 1, wherein the target tissue is within a human.

20. The method of claim 19, wherein the plurality of wavelengths comprises wavelengths from 725 nm to 880 nm.

21. The method of claim 1, wherein the target tissue is within an animal.

22. The method of claim 1, wherein the plurality of wavelengths comprises at least 100 wavelengths or more.

23. The method of claim 1, wherein the plurality of wavelengths comprises wavelengths from 700 nm to 1000 nm.

24. The method of claim 1, wherein the target tissue is a muscle tissue.

25. A method of monitoring blood volume in a patient, the method comprising:
directing incident radiation from a source to a target tissue of the patient and determining reflectance spectra of the target tissue with a detector by measuring intensities of reflected radiation from the target tissue at a plurality of wavelengths;
correcting the measured intensities of the reflectance spectra to reduce contributions thereto from skin and fat layers through which the incident radiation propagates;
determining total heme concentration in the target tissue based on the corrected reflectance spectra;
assessing a blood volume in the patient based on the total heme concentration; and
outputting the assessed blood volume,
wherein determining reflectance spectra of the target tissue comprises:
measuring, at a first source-detector spacing, a first reflectance spectrum from the target tissue that comprises a first weighting of contributions from the target tissue and from the skin and fat layers, and measuring, at a second source-detector spacing different from the first source-detector spacing, a second reflectance spectrum from the target tissue that comprises a second weighting of contributions from the target tissue and from the skin and fat layers different from the first weighting; and
wherein correcting the measured intensities of the reflectance spectra comprises:
correcting the measured intensities of the first reflectance spectrum based on the measured intensities of the second reflectance spectrum.

26. The method of claim 25, further comprising assessing a stage of progress of at least one of hemorrhage, sepsis, heart disease, and diabetes in the patient based on the assessed blood volume.

27. A method for calculating oxygen saturation in a target tissue, the method comprising:
directing incident radiation from a source to a target tissue and determining reflectance spectra of the target tissue with a detector by measuring intensities of reflected radiation from the target tissue at a plurality of radiation wavelengths;
determining light attenuation spectra of the target tissue from the reflectance spectra, and fitting the light attenuation spectra to a model light attenuation equation;
determining oxygen saturation in the target tissue based on the fitting of the light attenuation spectra; and
outputting the determined value of oxygen saturation,
wherein fitting the light attenuation spectra to a model comprises performing a two-stage fitting procedure wherein, in a first stage, initial values of one or more model parameters are determined, and in a second stage, the light attenuation spectra are fitted to the model, wherein the model comprises the initial parameter values determined in the first stage; and
wherein determining reflectance spectra of the target tissue comprises:
measuring, at a first source-detector spacing, a first reflectance spectrum from the target tissue that comprises a first weighting of contributions from the target tissue and from skin and fat layers through which the incident radiation passes, and measuring, at a second source-detector spacing different from the first source-detector spacing, a second reflectance spectrum from the target tissue that comprises a second weighting of contributions from the target tissue and from the skin and fat layers different from the first weighting; and
correcting the measured intensities of the first reflectance spectrum based on the measured intensities of the second reflectance spectrum.

28. The method of claim 27, wherein the model comprises a term having a functional form $a\lambda$ and wherein the value of $a$ is constrained during the fitting to be less than or equal to zero.

29. A system, comprising:
a light source configured to direct incident radiation to a target tissue;
a detector; and
a processor coupled to the detector and configured to:
determine reflectance spectra of the target tissue;
correct the reflectance spectra to reduce contributions thereto from skin and fat layers through which the incident radiation propagates; and
determine oxygen saturation in the target tissue based on the corrected reflectance spectra,
wherein the processor is configured to determine the reflectance spectra by:
measuring, at a first source-detector spacing, a first reflectance spectrum from the target tissue that comprises a first weighting of contributions from the target tissue and from skin and fat layers through which the incident radiation passes, and measuring, at a second source-detector spacing different from the first source detector spacing, a second reflectance spectrum from the target tissue that comprises a second weighting of contributions from the target tissue and from the skin and fat layers different from the first weighting; and
wherein the processor is configured to correct the reflectance spectra by:
correcting the measured intensities of the first reflectance spectrum based on the measured intensities of the second reflectance spectrum.

30. The system of claim 29, wherein the processor is configured to determine reflectance spectra of the target tissue by directing the detector to measure intensities of reflected radiation from the target tissue at a plurality of radiation wavelengths.

31. The system of claim 29, wherein the processor is configured to determine oxygen saturation by calculating light attenuation spectra from the corrected reflectance spectra, and calculating oxygen saturation based on concentrations of oxygenated and deoxygenated heme in the target tissue that are derived from the light attenuation spectra, wherein heme comprises hemoglobin and myoglobin in the target tissue.

32. The system of claim 31, wherein the processor is configured to derive the concentrations of oxygenated and deoxygenated heme in the target tissue by fitting the light attenuation spectra to a model light attenuation equation.

33. The system of claim 32, wherein the model light attenuation equation comprises a Beer's Law equation comprising terms that correspond to absorption of incident radiation by oxygenated heme, deoxygenated heme, and water in the target tissue.

34. The system of claim 31, wherein the processor is further configured to determine total heme concentration in the target tissue from the concentrations of oxygenated and deoxygenated heme in the target tissue.

35. The system of claim 34, wherein the processor is further configured to assess a blood volume in the target tissue based on the total heme concentration.

36. The system of claim 29, wherein the first and second source detector distances correspond to first and second radiation paths between the light source and the detector, and each of the first and second radiation paths comprises an optical fiber.

37. The system of claim 29, wherein the processor is further configured to determine oxygen tension in the target tissue from oxygen saturation.

* * * * *